(12) United States Patent
Wijay et al.

(10) Patent No.: US 8,465,551 B1
(45) Date of Patent: Jun. 18, 2013

(54) TEMPORARY PROSTATIC STENT FOR BENIGN PROSTATIC HYPERPLASIA

(76) Inventors: Bandula Wijay, Friendswood, TX (US); Omar Durrani, Houston, TX (US); Nandhika Wijay, Friendswood, TX (US)

( * ) Notice: Subject to any disclaimer, the term of this patent is extended or adjusted under 35 U.S.C. 154(b) by 2 days.

(21) Appl. No.: 13/135,548

(22) Filed: Jul. 9, 2011

(51) Int. Cl.
*A61F 2/04* (2006.01)

(52) U.S. Cl.
USPC ..................................... 623/23.64

(58) Field of Classification Search
USPC ............ 623/1.15–1.48, 23.64–23.7; 606/108, 606/198
See application file for complete search history.

(56) References Cited

U.S. PATENT DOCUMENTS

| | | | |
|---|---|---|---|
| 4,762,128 A | 8/1988 | Rosenbluth | |
| 4,893,623 A | 1/1990 | Rosenbluth | |
| 5,466,242 A * | 11/1995 | Mori | 606/198 |
| 6,494,908 B1 * | 12/2002 | Huxel et al. | 623/1.22 |
| 6,692,521 B2 * | 2/2004 | Pinchasik | 623/1.12 |
| 6,702,846 B2 * | 3/2004 | Mikus et al. | 623/1.22 |
| 6,716,252 B2 | 4/2004 | Lazarovitz et al. | |
| 6,991,596 B2 | 1/2006 | Whalen et al. | |
| 7,108,655 B2 | 9/2006 | Whalen et al. | |
| 7,141,038 B2 | 11/2006 | Whalen et al. | |
| 8,007,702 B2 * | 8/2011 | Gellman | 264/145 |
| 2003/0040803 A1 * | 2/2003 | Rioux et al. | 623/23.7 |
| 2006/0030934 A1 * | 2/2006 | Hogendijk et al. | 623/1.22 |
| 2006/0276909 A1 * | 12/2006 | Gellman | 623/23.66 |
| 2007/0106371 A1 * | 5/2007 | Datta et al. | 623/1.22 |
| 2008/0133025 A1 * | 6/2008 | Daignault et al. | 623/23.7 |
| 2008/0255679 A1 * | 10/2008 | Ward | 623/23.66 |
| 2009/0125120 A1 * | 5/2009 | McWeeney | 623/23.66 |
| 2009/0177288 A1 * | 7/2009 | Wallsten | 623/23.66 |
| 2009/0259294 A1 * | 10/2009 | Cully et al. | 623/1.22 |
| 2010/0131048 A1 * | 5/2010 | Schmid et al. | 623/1.22 |
| 2010/0241240 A1 * | 9/2010 | Willard et al. | 623/23.66 |

* cited by examiner

*Primary Examiner* — Suzette J Gherbi
(74) *Attorney, Agent, or Firm* — Kajane McManus

(57) ABSTRACT

This invention relates to a temporary indwelling prostatic stent which provides a passage for urine through the prostatic urethra and which enable the patient to void the bladder at will. This temporary prostatic stent consists of a coiled or braided made out of metal or plastic section which spans the prostatic urethra, wings composed of memory alloy allowing an anchoring means in the bladder, and an anchoring means below the external sphincter, and a retrieval string to facilitate removal of the stent from the patient.

24 Claims, 7 Drawing Sheets

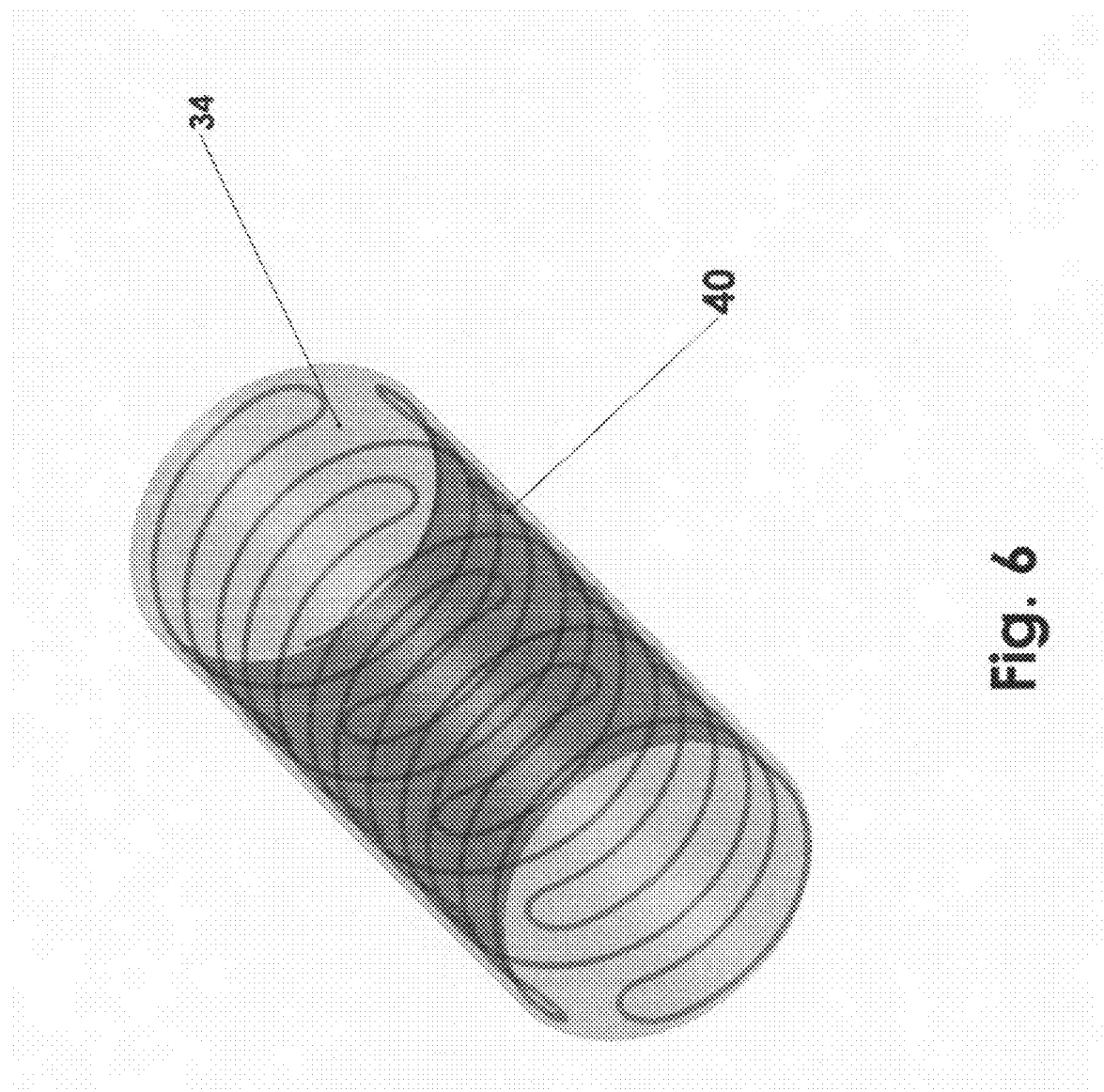

TEMPORARY PROSTATIC STENT FOR BENIGN PROSTATIC HYPERPLASIA

FIELD OF INVENTION

This invention relates to an endo-urethral device or more particularly a prostatic stent, for providing temporary relief arising from various causes such as benign prostatic hyperplasia.

BACKGROUND OF THE INVENTION

Urinary retention, a partial or complete inability to empty the bladder, can result from a variety of causes including benign prostatic hyperplasia (BHP), prostate cancer, bladder cancer, spinal cord injury, injuries of the urinary tract, urethral stricture, and urinary tract infection. If left untreated, urinary retention can have serious consequences for the patient including kidney failure. Therefore, patients with chronic or acute urinary retention usually require some type of intervention. A very common intervention is the insertion of an indwelling catheter, such as a Foley catheter, which provides a temporary conduit for draining the bladder. Because Foley catheters traverse the entire length of the urethra and include a segment that protrudes externally from the patient, these catheters are used only for temporary relief of acute or chronic urinary retention and especially for bladder drainage while patients are recovering from most types of surgeries.

Benign prostatic hyperplasia, the enlargement of the prostate gland, is the most common cause of bladder outlet obstruction. The prostate gland is about the size of a chestnut and surrounds the urethra just below the bladder neck. As men age, the prostate becomes larger, a process that constricts the urethra and obstructs the normal flow of urine from the bladder. Benign prostatic hyperplasia is very common and typically begins to develop in males older than 50. In fact, 60% of men over 60 and 95% of men over 80 experience bladder outlet obstruction due to BHP.

Surgical treatments are available which remove all or part of the prostate gland, thereby reducing or eliminating the urethral constriction and improving the patient's quality of life. These treatments include prostatectomy (open and laparoscopic), transurethral resection of the prostate (TURP), transurethral radiofrequency needle ablation (TUNA), transurethral microwave thermotherapy (TUMT), laser prostatectomy (LAP), and other experimental and emerging procedures. Open prostatectomy is the surgical removal of the inner portion of the prostate gland usually from a suprapubic or retropubic approach. Transurethral resection of the prostate (TURP) is considered the benchmark treatment for BHP and involves inserting a resectoscope and an electric loop to remove the obstructing tissue and to seal blood vessels. Transurethral radiofrequency needle ablation (TUNA) is a procedure in which low-level radiofrequency energy is delivered through needles to a localized area of the prostate, causing an increase in temperature, and inducing necrosis of prostatic tissue. Transurethral microwave thermotherapy (TUMT) uses microwave energy to heat prostatic tissue and simultaneously cools adjacent urethral tissue. Laser prostatectomy (LAP) is a minimally-invasive approach that uses laser-generated heat to vaporize or coagulate prostate tissue.

Recently, prostatic stents have been introduced as an alternative to surgical methods in the treatment of BHP. A prostatic stent, which was first developed in 1980, is a specialized urethral catheter that provides temporary or permanent relief of bladder outlet obstruction arising from BHP. The stents typically consist of a reinforced tubular section that spans the prostatic urethra, an anchoring means to keep it in place, and, in most cases, a tether for the removal of the stent. Unlike the Foley catheter, a prostatic stent does not typically include a section that extends externally from the patient. Prostatic stents are particularly useful for elderly patients or patients who are unable to undergo any of the typical surgical methods.

Several types of prostatic stents have been described in the prior art. Most of the early stent designs consist of a metal or plastic tube that spans the prostatic urethra providing an open conduit for urine drainage. For example, Rosenbluth, in U.S. Pat. Nos. 4,762,128 and 4,893,623 describes a metal prostatic stent that is deployed in the prostatic urethra via an inflatable balloon. These metal or plastic stents are not ideal for BHP because prostate and urethral tissue can become implanted in between the struts of the stent making them very difficult to remove without major surgery. In addition, these stents can lead to discomfort, inflammation, and infection. Other stent designs in the prior art consist of a plastic tube which spans, and is anchored within, the prostatic urethra. Even though these stents avoid the problems associated with metal stents, they can easily migrate or become dislodged, may cause discomfort for the patient, and may be difficult to remove. In addition, some of these stents are quite complex, expensive to make, and difficult to manufacture. Other anchoring methods have also been proposed for plastic stents that span the prostatic urethra, such as plastic stents with conical or flanged ends which are positioned immediately above and below the prostate so as to anchor the stent within the prostatic urethra.

In order to improve urinary drainage and patient comfort, other prostatic stent designs have been proposed. Unlike the previously mentioned designs, these stents span both the prostatic urethra and the external sphincter. Some of these stents do not have any anchoring means. As a result, there is a significant likelihood that these stents will migrate or become dislodged when voiding, cause discomfort, or leak due to the composition and dimension of the material that is placed in the narrow section that spans the external sphincter.

Since Foley catheters are used frequently to help with urine drainage, and since Foley catheters are equipped with an inflatable balloon that functions as an anchoring means within the bladder, many prostatic stent designs have adopted the inflatable balloon feature as well. For instance, Lazarovitz et al. in U.S. Pat. No. 6,716,252 describes a prostatic stent that spans the prostatic urethra and is equipped with an inflatable balloon which acts as an anchor within the bladder. This stent also includes a conical end that is placed immediately above the external sphincter which prevents the stent from migrating into the bladder. Whalen et al. in U.S. Pat. No. 7,141,038 describes a prostatic stent with a balloon anchor for the bladder, a compressible segment that spans the external sphincter, and another balloon that acts as an anchor in the penile urethra just below the external sphincter. This stent could be uncomfortable for the patient and would create severe problems and distress for the patient if either of the balloons malfunctioned.

Other recent prostatic stent designs include a balloon anchor for the bladder and another anchoring means immediately below the external sphincter in order to keep the stent properly positioned within the patient. For example, Whalen, et al., in U.S. Pat. Nos. 6,991,596 and 7,108,655 describe a prostatic stent with a balloon anchor in the bladder, a rigid section that spans the prostatic urethra, a series of threads that span the external sphincter, and an anchoring means immediately below the external sphincter. These stents are complex, expensive, and difficult to manufacture.

SUMMARY OF THE INVENTION

The present invention relates to a prostatic stent which provides temporary relief of urinary tract retention arising from conditions such as benign prostatic hyperplasia and which overcomes the limitations and drawbacks of Foley catheterization. This prostatic stent facilitates bladder drainage by providing an open passageway in the prostatic urethra while leaving the external sphincter unhindered so that the patient can control urination in a normal fashion. The prostatic stent of the present invention is a partial-length indwelling device which is anchored in the bladder neck and which spans the prostatic urethra, thereby providing a means to open the prostatic urethra in order to facilitate drainage of urine from the bladder. The prostatic stent consists of coil (in which alternating coil segments are displaced such that the rungs of the coil protrude outward alternatively, thereby generating a ribbed surface) or a wire braid having an annular space and having a similar surface therein encased in silicone or a suitable polymeric sheath which is placed in the prostatic urethra upstream from the external sphincter and which facilitates an interior passageway, establishing fluid communication from the bladder to the penile urethra. The coil, as well as the braided tube with undulations of its outer surface, helps to anchor the prostatic stent in the prostatic urethra. The prostatic stent also has a proximal anchor that is placed within the bladder, which consists of two or more wings composed of memory alloy at its proximal end which protrude outward and which helps to anchor the stent in the bladder. The wings are shaped in such a manner that the distal tip of the wing, at its outer most edge, is slightly bent inwards, so that when the wings are pulled radially inwards using a retrieval string mechanism (to be described later), the string force action causes the wings to fold inwards, thereby causing a folded structure (of the stent) in order to gain a low profile enabling the stent to be removed from the prostrate easily. A distal anchor consisting of a flat zigzag wire form encased in silicone and having a flattened elliptical structure anchors the stent distally in the bulbous urethra, downstream of the external sphincter. This distal anchor prevents inward movement of the prostatic stent into the bladder. A retrieval string is attached to the very distal end of one of the said wings and is looped around the opposite wing(s) at least once, if not several times, so that when force is applied to the string, the wings fold as previously mentioned. The string then passes through the stent through the urethra to position just outside the penile urethra. Therefore, when the retrieval string is pulled, force is acted on both wings causing the wings to fold inwards, allowing for easy removal of the prostatic stent. If the string is looped more than one loop around between the wings, the force required to fold the wings will be reduced significantly due to the mechanical advantage.

The stent portion of the embodiment can be a spring coil, helical in shape or it can be a combination of helical-coils that are left and right handed. The stent can be either meshed or unmeshed or the structure can be in the form of a braid, without departing from the essence of this invention. The coils and wings will be made from memory alloys. However other materials such as stainless steel with a spring temper may also be used in order to keep the stent firmly pressed against the wall of the prostatic urethra. The distal ends of the wing, which is a wire bent in to inverted "U" shape, is threaded into the loops of the coil in order to offset the loops to achieve a form, where the loops project outwardly to create a surface that has undulations which will enhance the radial spring force of the stent to stay anchored in the prostatic urethra.

BRIEF DESCRIPTION OF THE DRAWINGS

FIG. 6 is another embodiment of the flexible stent body.

DETAILED DESCRIPTION OF THE PREFERRED EMBODIMENT

Figure 1:
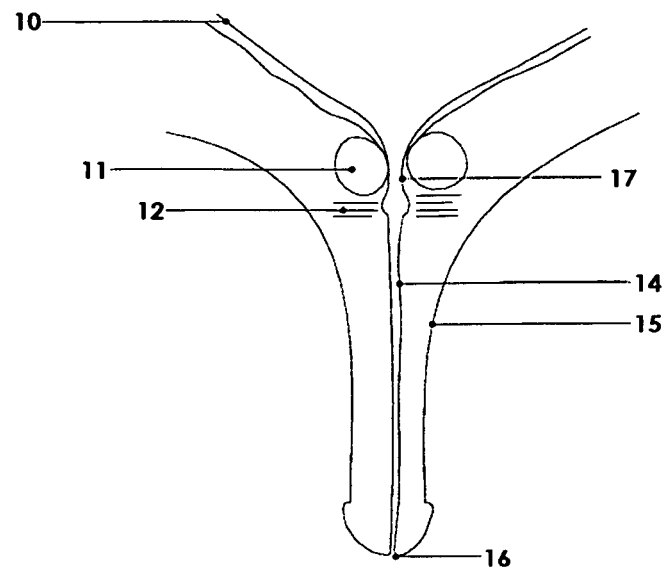
FIG. 1 shows the anatomy of the lower urinary tract of the human male.

FIG. 1 shows the anatomy of the lower urinary tract of the human male. The lower urinary tract consists of the bladder (10), the prostate (11), which is just below the bladder (10) and which surrounds the prostatic urethra (17), the external sphincter (12), the penile urethra (14) which extends through the penis (15), and the urethra opening (16) and the tip of the penis (15).

Figure 2:
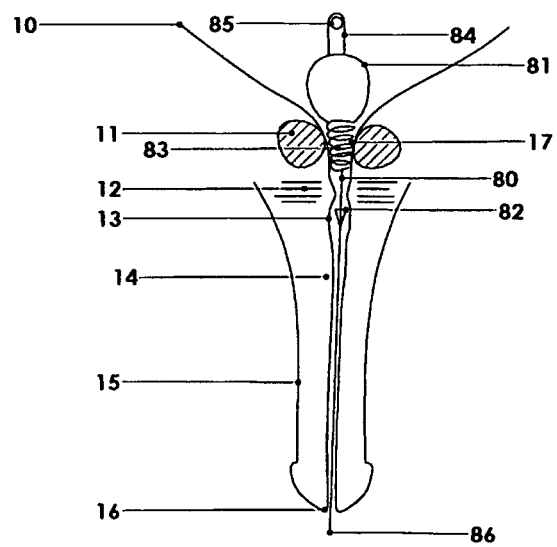
FIG. 2 shows a typical prostatic stent within the lower urinary tract of the human male (prior art).

FIG. 2 depicts a prostatic stent (80) in the prior art. This prior art prostatic stent (80) consists of a coil section (83) that spans the prostatic urethra (17) and which provides an open conduit between the bladder (10) and the penile urethra (14). An inflatable balloon (81) is used to anchor this prior art prostatic stent (80) in the bladder (10). The proximal end (84) of the prostatic stent (80) has a number of drainage holes (85) which are in communication with the lumen of the prostatic stent (80) to allow passage of urine from the bladder (10) to the outside of the body. An anchoring means (82), typically a triangular piece of silicone that is attached to the retrieval string, anchors this prior art prostatic stent (80) below the external sphincter (12) so that it does not migrate into the bladder (10). A retrieval string (86) provides a means to remove the prostatic stent (80) from the patient.

Figure 3A:
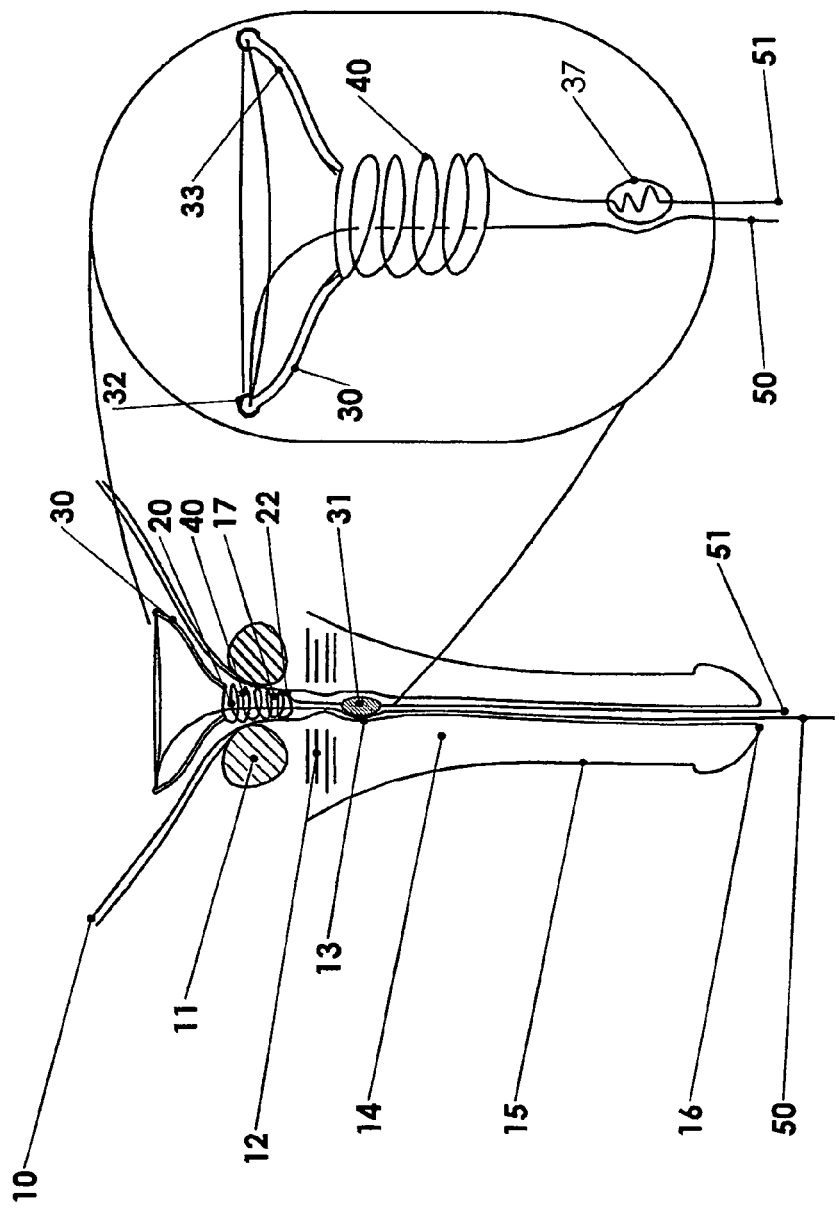
FIG. 3A shows the prostatic stent of the current invention within the lower urinary tract of the human male.

FIG. 3A depicts the prostatic stent (20) of the present invention in the lower urinary tract of the human male. The prostatic stent (20) consists of a wire form, the stent body portion (40). The wire form (40) of the prostatic stent (20) spans the prostatic urethra (17), and when placed in the patient, provides a conduit for urine drainage through the prostate (11) between the bladder (10) and bulbous urethra (13) while also helping to anchor the prostatic stent (20) within the prostatic urethra (17). The stent body, or the wire form (40) can be a simple helical coil, a coil formed with undulations on its outer surface, a braid or a braid with undulations on its outer surface.

Two wings (30) which are composed of a memory alloy wire loop extending from the coil (40) and provide the anchoring means within the bladder (10). When placed within the bladder (10) of the patient, the wings (30) of the prostatic stent (20) relax to their shape memory configuration by bowing outward, thereby anchoring the prostatic stent (20) within the bladder (10). A retrieval string (50) is threaded through the wings (30) and when it is pulled, pulls the wings (30) together so that the prostatic stent (20) can be removed from the patient. The wings (30) are provided with a bend (33) so that when tension is applied on to the wings (30), it causes the wings (30) to bend easily and fold inwards. The string 50 acts as an actuator member for placement or removal of the stent 20.

In order to prevent migration of the stent into the bladder (10), a distal anchor (31) consisting of a zigzag metal form, encased in silicone, and which has a flattened elliptical structure, is attached to a string (51) which is attached the proximal end (22) of the stent body, the wire form (40). The distal anchor (31) is positioned downstream from the wire form (40) and the external sphincter (12). The retrieval string (50) extends from the wings (30), through the stent body (40), and through the penile urethra (14) of the penis (15), extending past the urethral orifice (16).

Figure 3B:
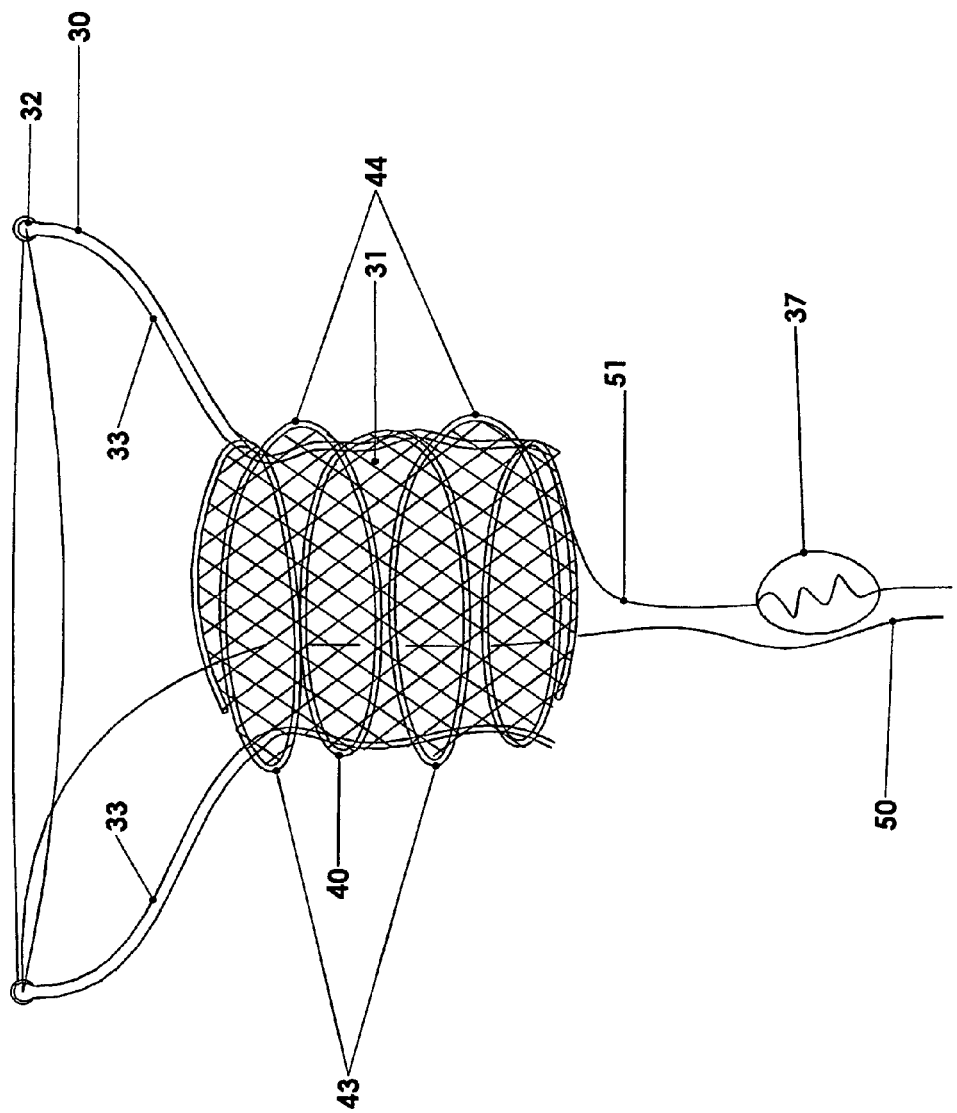
FIG. 3B shows one embodiment of the coil consisting of single coil encased in a polymetric sheath.

FIG. 3B shows the detail to one embodiment of the stent body (40) of prostatic stent (20). The wings (30) are bowed outward and have a bend (33), providing an anchoring means within the bladder (10). The retrieval string (50) is threaded through the holes (32) at the distal tips of the wings (30) with one or more loops. The stent body or the wire form (40), which can be a coil or yet another form, spans the prostatic urethra (17), providing a conduit for urine drainage between the bladder (10) and the bulbous urethra (13), and anchoring the prostatic stent (20) within the prostatic urethra (17). The stent body (40) is encased in a polymeric sheath (31) which can be composed of silicone, Teflon, polyester, nylon, or any other suitable biomaterial. The string (51) that attaches the proximal anchor to the alternating loop coil of the stent body (40) is also shown.

Figure 3C:
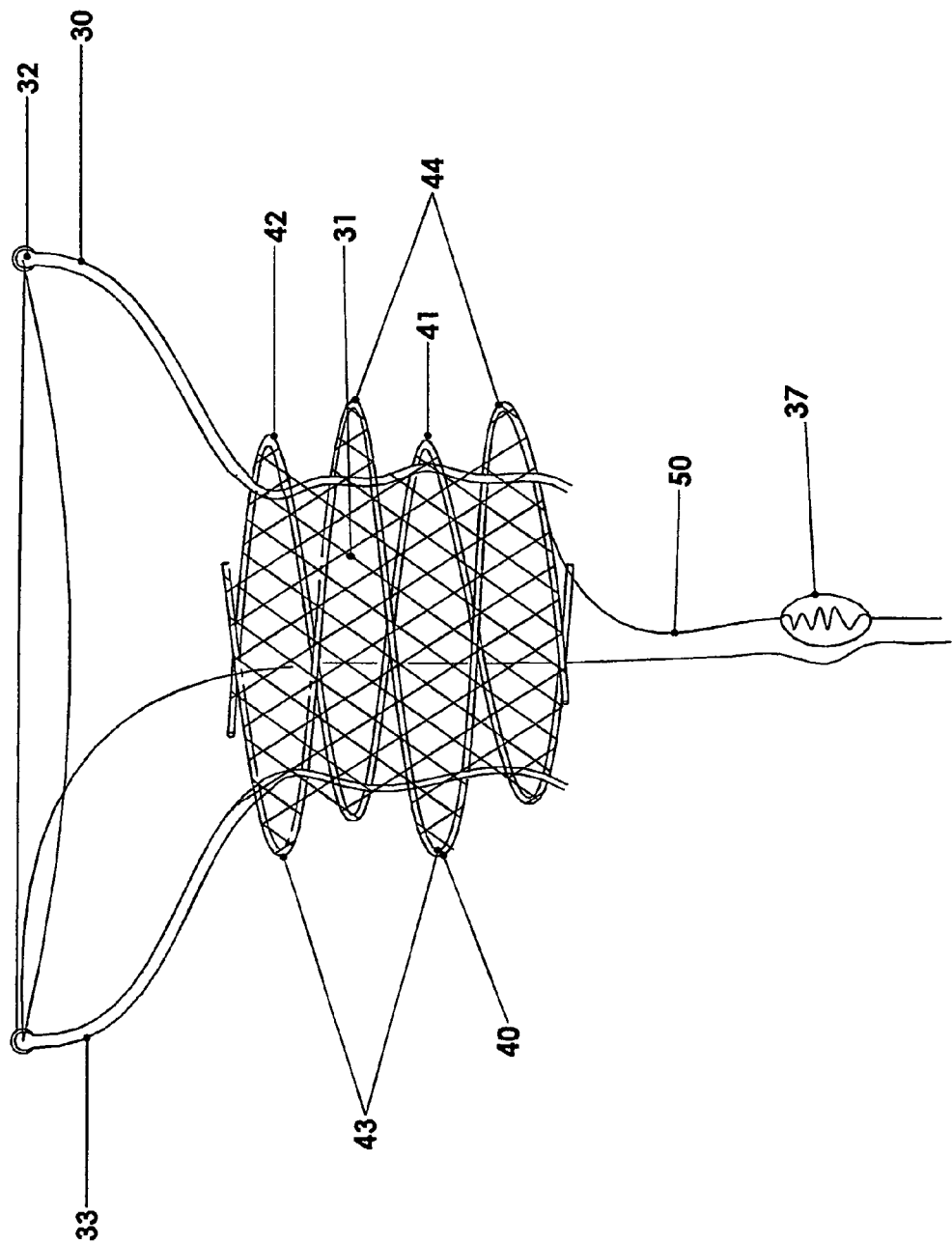
FIG. 3C shows another embodiment of the coil consisting of two coils or a braid encased in a polymetric sheath.
Figure 4:
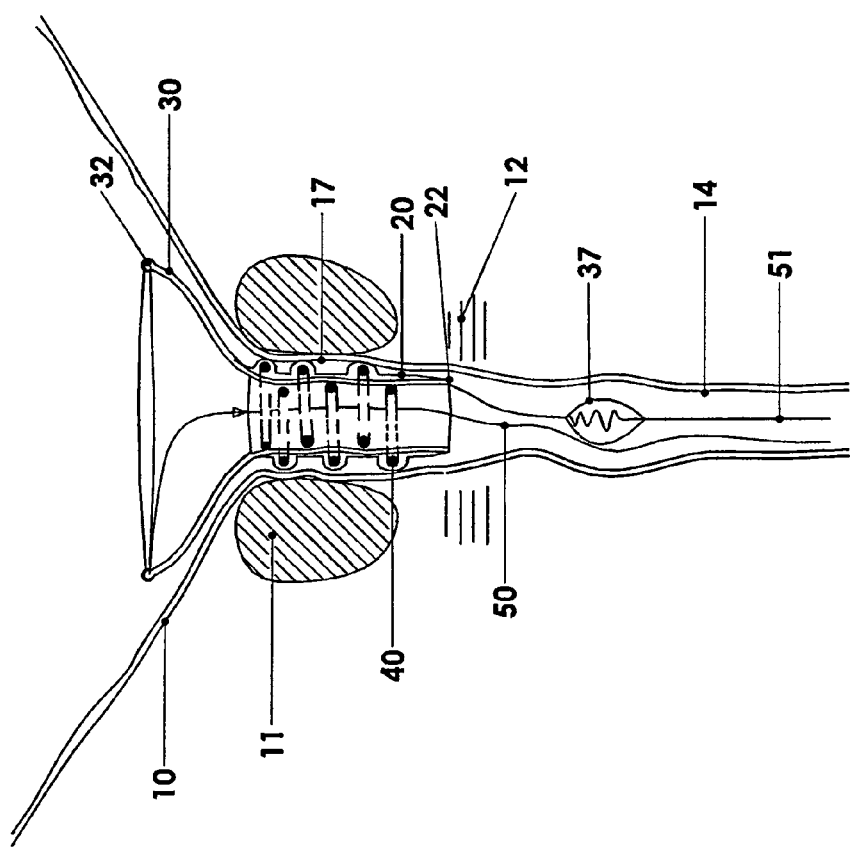
FIG. 4 shows a detailed view of the prostatic stent of the current invention within the lower urinary tract of the human male.

FIG. 3C shows another embodiment of the stent body or the wire form (40) of the prostatic stent (20). The wings (30) are bowed outward, providing an anchoring means within the bladder (10). The retrieval string (50) is threaded through the holes (32) at the distal tips of the wings (30). The stent body (40) spans the prostatic urethra (17), providing a conduit for urine drainage between the bladder (10) and the bulbous urethra (13), and anchoring the prostatic stent (20) within the prostatic urethra (17). The stent body (40) can consist of two coils (41 and 42) in opposite directions, left hand and right hand, or it can also be a braid. The stent body (40) is encased in a polymeric sheath (31) which can be composed of silicone, Teflon, polyester, nylon, or any other suitable biomaterial. The stent has undulations (44) on its outer surface as shown in FIG. 3C FIG. 4 shows a detailed view of the prostatic stent (20) within the lower urinary tract of the human male. The retrieval sting (50) is threaded through the holes (32) at the tips of the wings (30), and one end of the retrieval string (50) is attached to one of the holes (32) of the wings (30). The retrieval string (50) is threaded through the stent body (40), through the penile urethra (14), extending out of the penis (15). The string (51) attaches the distal anchor (37) to the proximal end (22) of the stent body (40) and also exits the urethra.

Figure 5:
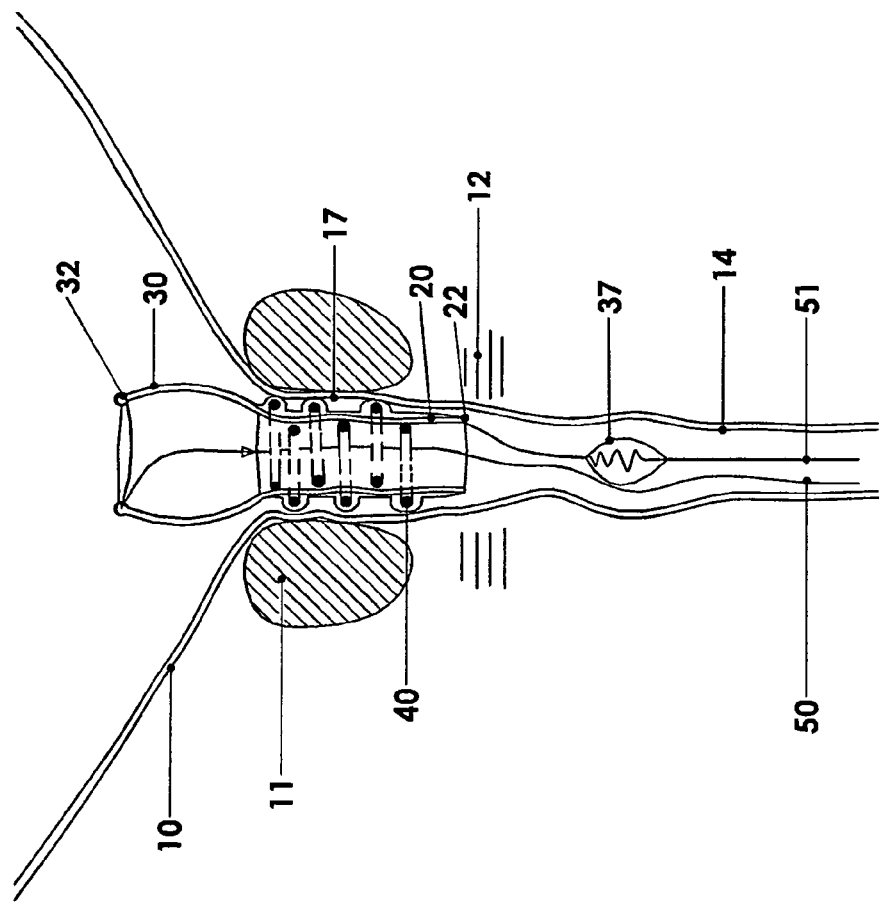
FIG. 5 shows the removal of the prostatic stent of the current invention from the lower urinary tract of the human male.

FIG. 5 shows the removal of the prostatic stent (20) from the lower urinary tract of the human male. When the retrieval string (50) is pulled, the wings (30) are pulled together to fold the wings, thereby reducing its profile thus allowing the prostatic stent (20) to be removed from the patient easily.

FIG. 6 shows an alternate embodiment for the flexible stent body (40) which is a nested loop cylinder, where loops of wire, preferably of shape memory alloy, alternate forming a cylindrical tube shape. The loop ends of each loop is separated or offset by an angle greater than 1 degree. The most preferable angle is 180 degrees, in which case the loops are diagonally opposite. As in previous examples, this flexible stent body (40) may also be enclosed in a polymeric sheath (34).

We claim:

1. A prostatic stent, comprising:
a flexible stent body defining a passage therethrough;
a first and a second anchor, said anchors disposed adjacent opposed ends of said stent body;
said first anchor comprising at least one flexible elongated cantilevered member disposable in the bladder for bladder contact along the length of said member to retain said stent with respect to the bladder by virtue of extension into said bladder in the same general direction as said body;
said stent body comprises at least one coil or wire braid;
said coil is made from a continuous filament wound into a plurality of open ring shapes having circumferentially offset gaps.

2. The stent of claim 1, wherein:
said first anchor having a relaxed position misaligned with the penile urethra and a removal position that is substantially aligned with the penile urethra.

3. The stent of claim 2, wherein:
an actuating member engaged to said flexible elongated member for remotely moving said flexible elongated member between said relaxed and said removal positions.

4. The stent of claim 3, wherein:
said at least one flexible elongated member comprises a plurality of flexible elongated members.

5. The stent of claim 4, wherein:
said plurality of flexible elongated members has free ends extending radially beyond an outer dimension of said stent.

6. The stent of claim 5, wherein:
said elongated members extend from said stent and further comprise a curvature between said stent and said free end.

7. The stent of claim 6, wherein:
said actuating member connecting at least two said free ends to selectively bring said flexible elongated members into general alignment with the penile urethra for removal of said stent.

8. The stent of claim 7, wherein:
said flexible elongated members comprising a loop at said free end thereof for engagement of said actuating member.

9. A prostatic stent, comprising:
a flexible stent body defining a passage therethrough;
a first and a second anchor, said anchors disposed adjacent opposed ends of said stent body;
said first anchor comprising at least one flexible elongated member disposable in the bladder to retain said stent with respect to the bladder;
said first anchor having a relaxed position misaligned with the penile urethra and a removal position that is substantially aligned with the penile urethra;
an actuating member engaged to said flexible elongated member for remotely moving said flexible elongated member between said relaxed and said removal positions;
said at least one flexible elongated member comprises a plurality of flexible elongated members;
said plurality of flexible elongated members has free ends extending radially beyond an outer dimension of said stent;
said elongated members extend from said stent and further comprise a curvature between said stent and said free end;
said actuating member connecting at least two said free ends to selectively bring said flexible elongated members into general alignment with the penile urethra for removal of said stent;

said flexible elongated members comprising a loop at said free end thereof for engagement of said actuating member;

said actuating member comprises a thread extending through loops of said elongated members and through said stent such that tension on said thread brings said free ends toward each other.

10. The stent of claim 9, wherein:
said stent defines undulations along its length.

11. The stent of claim 10, wherein:
said stent body comprises at least one coil or wire braid.

12. A prostatic stent, comprising:
a flexible stent body defining a passage therethrough;
a first and a second anchor, said anchors disposed adjacent opposed ends of said stent body;
said first anchor comprising at least one flexible elongated member disposable in the bladder to retain said stent with respect to the bladder;
said stent defines undulations along its length;
said stent body comprises at least one coil or wire braid;
said at least one coil comprises a plurality of coils with at least two having opposed windings.

13. The stent of claim 12, wherein:
said second anchor comprising a flattened elliptical shape connected to the said stent by a flexible member.

14. The stent of claim 12, wherein:
at least one of said stent and said first anchor are coated with a polymeric biocompatible material.

15. The stent of claim 14, wherein:
said bio-compatible material further comprises a therapeutic agent.

16. The stent of claim 9, wherein:
said stent defines undulations along its length.

17. The stent of claim 16, wherein:
said stent comprises at least one coil or wire braid.

18. The stent of claim 17, wherein:
said at least one coil comprises a plurality of coils with at least two having opposed windings.

19. The stent of claim 17, wherein:
said second anchor comprising a flattened elliptical shape connected to the said stent by a flexible member.

20. The stent of claim 17, wherein:
at least one of said stent and said first anchor are coated with a polymeric biocompatible material.

21. The stent of claim 17, wherein:
said bio-compatible material further comprises a therapeutic agent.

22. A prostatic stent comprising:
a flexible stent body defining a passage therethrough;
a first and a second anchor, said anchors disposed adjacent opposed ends of said stent body;
said first anchor comprising at least one flexible elongated member disposable in the bladder to retain said stent with respect to the bladder;
said stent defines undulations along its length;
said stent body comprises at least one coil or wire braid;
said coil is made from a continuous filament wound into a plurality of open ring shapes having circumferentially offset gaps.

23. The stent of claim 22, wherein:
said ring shapes comprise spaced substantially parallel runs of said filament.

24. The stent of claim 1, wherein:
said elongated cantilevered member having an end extending away from a wall defining the bladder.

* * * * *